United States Patent
Want et al.

(10) Patent No.: US 6,902,550 B2
(45) Date of Patent: Jun. 7, 2005

(54) SYSTEM FOR DRAINING FLUIDS

(75) Inventors: Nicholas Want, Manchester, NH (US); Theodore Karwoski, Hollis, NH (US)

(73) Assignee: Atrium Medical Corporation, Hudson, NH (US)

( * ) Notice: Subject to any disclaimer, the term of this patent is extended or adjusted under 35 U.S.C. 154(b) by 105 days.

(21) Appl. No.: 10/162,982

(22) Filed: Jun. 5, 2002

(65) Prior Publication Data

US 2002/0198505 A1 Dec. 26, 2002

Related U.S. Application Data

(60) Provisional application No. 60/295,964, filed on Jun. 5, 2001.

(51) Int. Cl.$^7$ .................................................. A61M 1/00
(52) U.S. Cl. ...................................... 604/321; 604/540
(58) Field of Search ................................. 604/317–332, 604/411, 414, 415, 313–316, 540–544; 4/144.1, 144.2, 144.3, 144.4

(56) References Cited

U.S. PATENT DOCUMENTS

| | | | |
|---|---|---|---|
| 3,502,086 A | * | 3/1970 | Karwoski et al. ............ 131/205 |
| 3,937,219 A | | 2/1976 | Karakashian |
| 4,112,948 A | | 9/1978 | Kurtz et al. |
| 4,137,579 A | * | 2/1979 | Soler .............................. 4/311 |
| 4,440,327 A | | 4/1984 | Dark |
| 4,605,400 A | | 8/1986 | Kurtz et al. |
| 4,619,647 A | | 10/1986 | Kurtz et al. |
| 4,648,874 A | | 3/1987 | Kurtz et al. |
| 4,675,011 A | | 6/1987 | Kurtz et al. |
| 4,811,847 A | | 3/1989 | Reif et al. |
| 4,878,903 A | | 11/1989 | Mueller |
| 4,954,239 A | | 9/1990 | Mueller |
| 5,185,007 A | * | 2/1993 | Middaugh et al. ........... 604/320 |
| 5,217,038 A | | 6/1993 | Pinder |
| 5,380,314 A | * | 1/1995 | Herweck et al. ............. 604/403 |
| 5,392,968 A | | 2/1995 | Dark |
| 5,401,262 A | * | 3/1995 | Karwoski et al. ............ 604/321 |
| RE35,225 E | * | 4/1996 | Herweck et al. ............. 604/321 |
| 5,807,358 A | | 9/1998 | Herweck et al. |
| 5,807,359 A | * | 9/1998 | Bemis et al. ................ 604/322 |
| 6,210,383 B1 | | 4/2001 | Want et al. |
| 6,261,276 B1 | * | 7/2001 | Reitsma ....................... 604/319 |
| 6,358,232 B1 | * | 3/2002 | Hand et al. .................. 604/319 |
| 6,494,869 B1 | * | 12/2002 | Hand et al. .................. 604/319 |
| 6,558,365 B2 | * | 5/2003 | Zinger et al. ................ 604/410 |
| 6,706,031 B2 | * | 3/2004 | Manera ........................ 604/411 |
| 2002/0182718 A1 | * | 12/2002 | Malmquist ................ 435/287.2 |
| 2002/0193777 A1 | * | 12/2002 | Aneas ........................ 604/411 |

OTHER PUBLICATIONS

Case History: Packaging Line Dries the Tears, Pharmaceutical & Medical Packaging News, 2000.
Rommelag AG, Printed Information on BOTTELPACK, undated.

* cited by examiner

*Primary Examiner*—Larry I. Schwartz
*Assistant Examiner*—Michael G Bogart
(74) *Attorney, Agent, or Firm*—RatnerPrestia (57) ABSTRACT

A kit for draining fluids from the body of a patient is provided. The kit eliminates the problem of having to obtain a distinct liquid source and a means for delivering the liquid into a chamber of a chest drain. The kit includes an apparatus configured to receive fluids from the body of the patient. The apparatus defines a chamber to contain a predetermined volume of liquid. The apparatus includes an inlet through which liquid is deliverable to the chamber of the apparatus from an exterior of the apparatus. The kit also includes a container packaged with or attached to the apparatus. The container is prefilled and sealed to contain at least the predetermined volume of liquid. The container includes an outlet configured to deliver at least the predetermined volume of liquid to the chamber of the apparatus through the inlet of the apparatus.

21 Claims, 9 Drawing Sheets

SYSTEM FOR DRAINING FLUIDS

This application claims the benefit of Provisional application Ser. No. 60/295,964, filed Jun. 5, 2001.

TECHNICAL FIELD

The present invention relates, in general, to fluid drainage systems, and more specifically, to chest drainage systems.

BACKGROUND OF THE INVENTION

Chest drains are often used in connection with cardiac and thoracic surgical procedures in order to remove fluids from the chest cavity of a patient. Suction is typically used to draw fluid into the chest drain. Such chest drains frequently include a water seal in order to prevent the back flow of fluid (primarily gases) through the chest drain and back toward the patent's chest cavity. Such water seals therefore permit withdrawal of fluids from the patient while preventing the return of fluids back toward the patient through the chest drain.

Chest drains that include a water seal are provided with a water seal chamber, which is configured to hold a predetermined or pre-specified volume of liquid, such as water or saline, that creates the seal. When used, the water seal chamber is filled with liquid by a medical professional.

Figure 1:
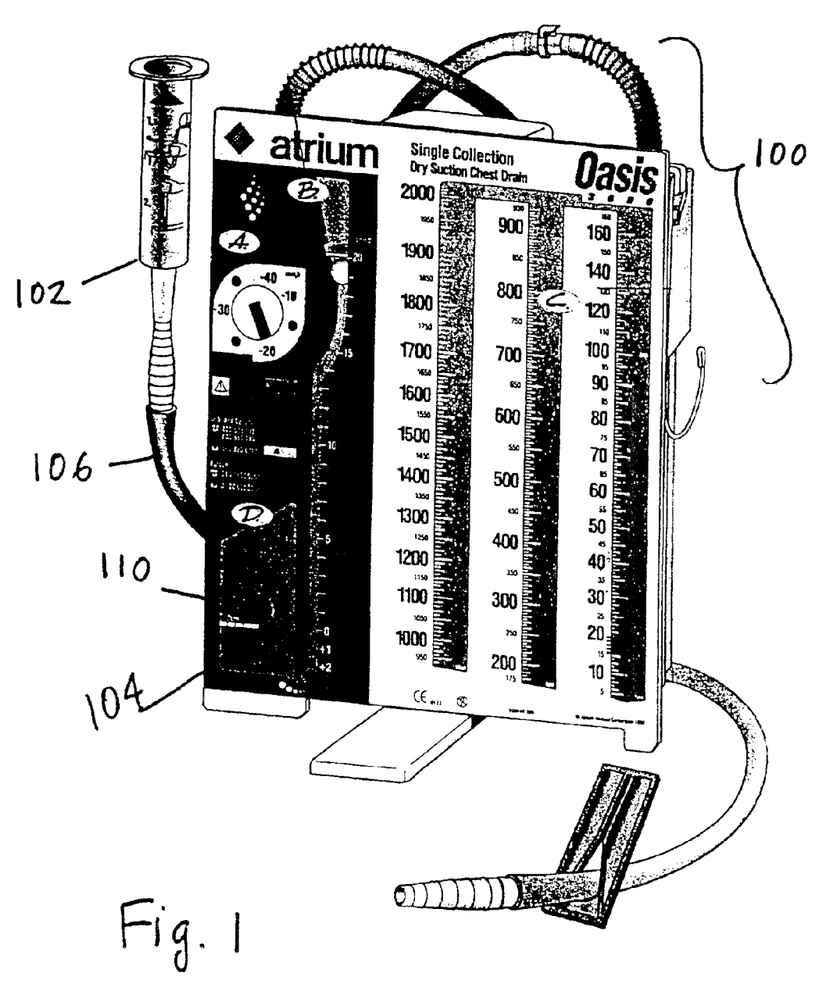
FIG. 1 is a perspective view of a chest drain including a fluid chamber filled with a funnel.

A funnel can be used to fill the water seal chamber of a chest drain. Referring to FIG. 1, for example, the OASIS™ 3600 Chest Drain of Atrium Medical Corporation is shown. Exemplary features of the OASIS™ product are described by Herweck et al. in U.S. Pat. No. 5,807,358, which is incorporated herein by reference. As shown in FIG. 1, a pre-attached funnel 102 can be used to introduce water into the water seal chamber 104 of the chest drain 100.

Figure 2:
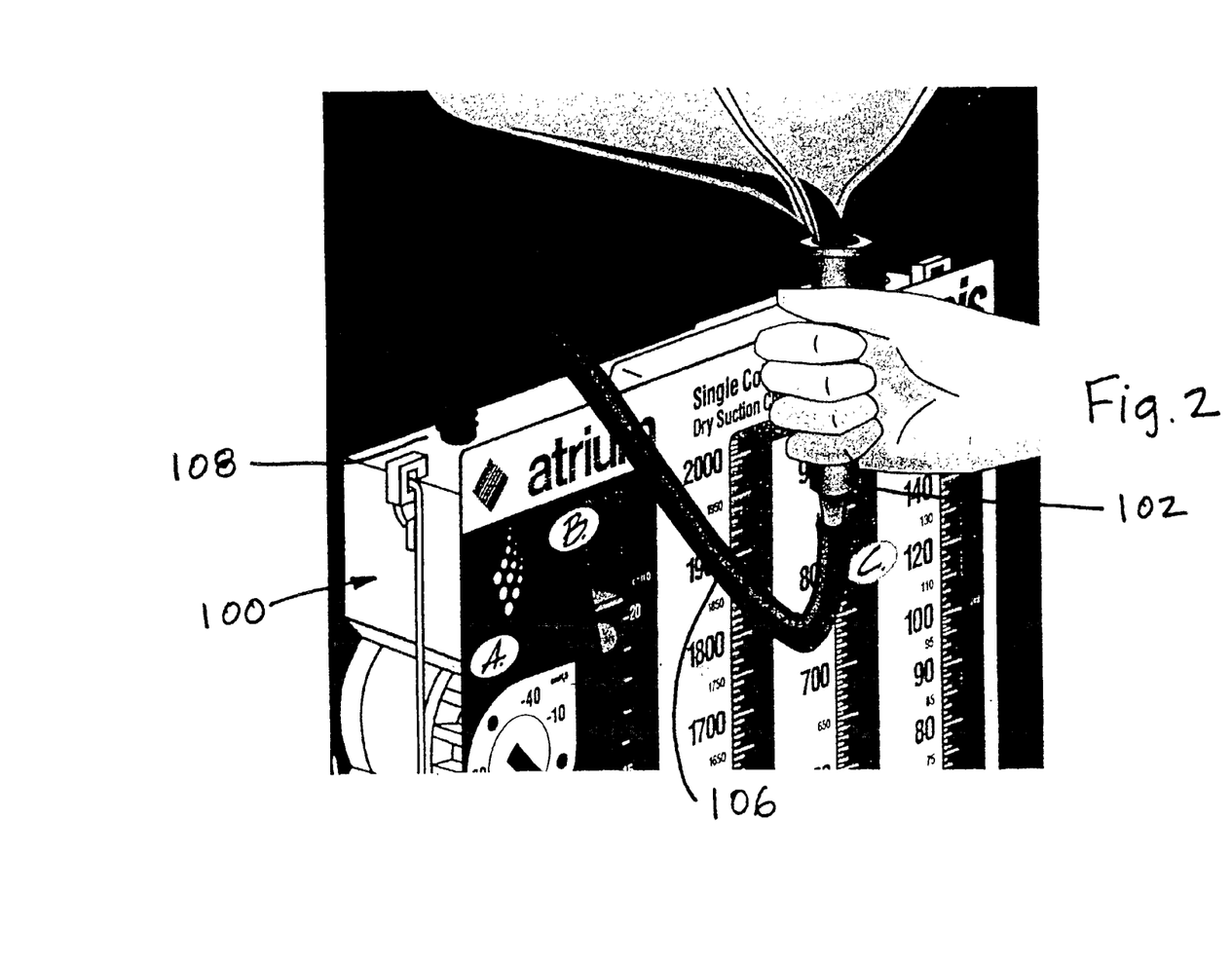
FIG. 2 is a partial perspective view of the chest drain of FIG. 1.

More specifically, referring to FIG. 2, a funnel 102 is attached via tubing 106 to an inlet 108 at the top of the chest drain 100. The funnel 102 is positioned as shown and water is added to the top of the funnel 102. The funnel 102 is then raised to empty the water into the water seal chamber 104 to a desired level, fill line 112 (i.e., the 2 cm fill line shown in FIG. 1 below the label "D"), that corresponds to a predetermined volume. If the water seal chamber 104 is overfilled, a syringe needle (not shown in FIG. 2) can be used to remove excess water through the self-sealing grommet 110 provided above the fill line. Accordingly, the funnel approach involves obtaining a source of water, filling the funnel 102, and (if necessary) using a syringe to remove excess water through the self-sealing grommet 110. This tedious process of obtaining the source of water, filling the funnel 102 and subsequently the water seal chamber, and removing excess water may be inconvenient for a medical professional in certain circumstances.

Figure 3:
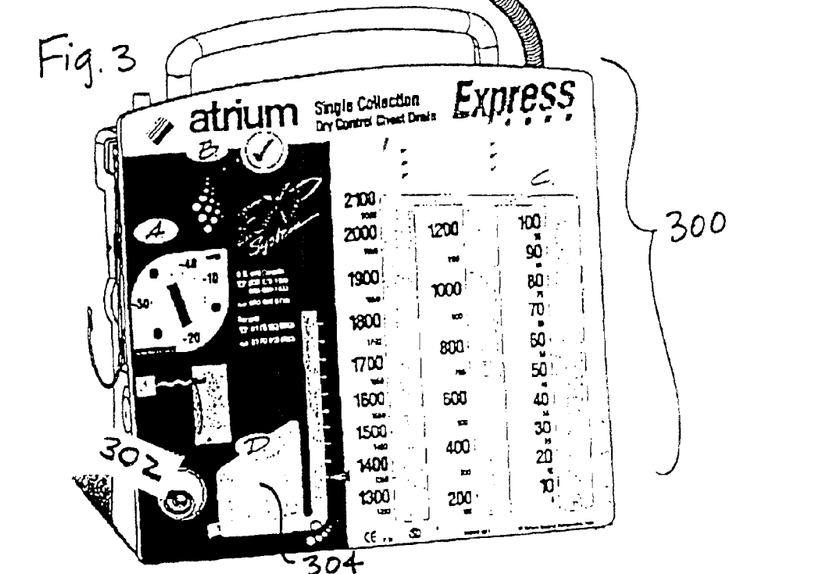
FIG. 3 is a perspective view of a chest drain including a needleless access port for filling a fluid chamber.

Referring to FIG. 3, a needleless access port 302 can also be used to fill the water seal chamber 304 of a chest drain 300. For example, the EXPRESS™ 4000 Chest Drain of Atrium Medical Corporation is shown in FIG. 3. Exemplary features of the EXPRESS™ product are described by Want et al. in U.S. Pat. No. 6,210,383, which is incorporated herein by reference. A needleless access port 302 is provided on the chest drain 300 (shown next to the water seal chamber 304 and the label "D" in FIG. 3), and the needleless access port 302 is used to introduce water into the water seal chamber 304.

Figure 4:
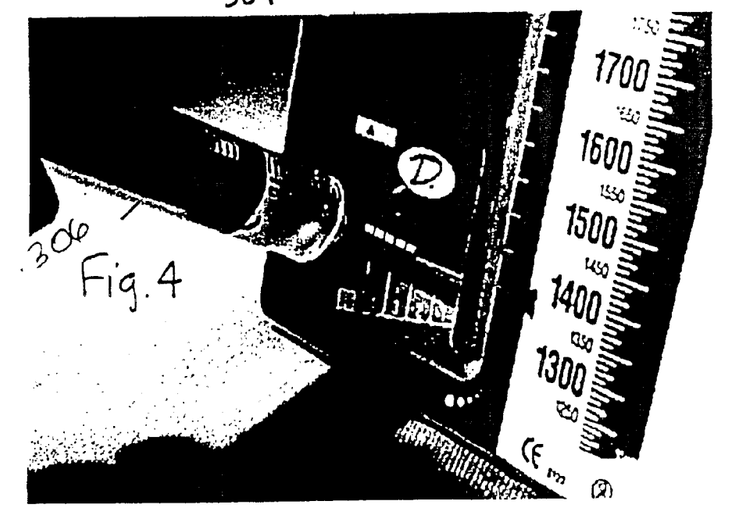
FIG. 4 is a partial perspective view of the chest drain of FIG. 3.

Referring to FIG. 4, which illustrates details of the chest drain shown in FIG. 3, a luer-lock syringe 306 is used by a medical professional to introduce liquid into the water seal chamber 304 through the needleless access port 302. This involves filling the syringe 306 with an appropriate amount of water (or other liquid) so that it can be introduced into the water seal chamber 304. It is, however, sometimes inconvenient for medical professionals to (1) access a supply of appropriate water; (2) obtain a properly sized syringe 306; (3) fill the syringe 306 with water and introduce the water through the needleless access port 302; and (4) confirm that the amount of water introduced into the water seal chamber 304 is proper. If the water seal chamber 304 is overfilled, a syringe can be used to withdraw the excess water. Such a system can be especially inconvenient because, when a syringe 306 is desired for use with the chest drain 300, an appropriate syringe 306 must be located and filled by the medical professional. As such, inefficiency and inconvenience exists in the setup of the chest drain 300.

Whether the funnel approach or needleless access port approach is used for filling the water seal chamber, the performance of the chest drain and the water seal may vary depending upon whether the water seal chamber is filled with the appropriate volume of water. More specifically, if the water seal chamber is overfilled or underfilled, then the intended performance of the water seal may not be achieved. Accordingly, the medical professional should check the level of water in the water seal chamber and supplement the water to raise the level or withdraw excess water to lower the level.

SUMMARY OF THE INVENTION

To meet this and other needs, and in view of its purposes, one exemplary embodiment of the present invention provides a kit for draining fluids from the body of a patient. The kit includes an apparatus configured to receive fluids from the body of the patient. The apparatus defines a chamber to contain a predetermined volume of liquid. The apparatus also includes an inlet through which liquid is deliverable to the chamber of the apparatus from an exterior of the apparatus. The kit also includes a container packaged with or attached to the apparatus. The container is prefilled and sealed, and contains at least the predetermined volume of liquid. The container includes an outlet configured to deliver at least the predetermined volume of liquid to the chamber of the apparatus through the inlet of the apparatus.

In another exemplary embodiment of the present invention, a method of providing or obtaining a kit for draining fluids from the body of a patient is provided. The method includes a step of providing an apparatus configured to receive fluids from the body of the patient. The apparatus provided defines a chamber to contain a predetermined volume of liquid. The apparatus provided also includes an inlet through which liquid is deliverable to the chamber of the apparatus from an exterior of the apparatus. The method also includes the step of packaging a container with the apparatus. The container packaged with the apparatus is prefilled and sealed to contain at least the predetermined volume of liquid. The container packaged with the apparatus also includes an outlet configured to deliver at least the predetermined volume of liquid to the chamber of the apparatus through the inlet of the apparatus.

In yet another exemplary embodiment of the present invention, a method of preparing a system for draining fluids from the body of a patient is provided. The method includes a step of obtaining a kit including an apparatus configured to receive fluids from the body of the patient. The apparatus included in the obtained kit defines a chamber to contain a predetermined volume of liquid. The kit obtained also includes a container packaged with or attached to the apparatus. The container is prefilled and sealed to contain at least the predetermined volume of liquid. The method also includes a step of delivering the predetermined volume of liquid from the container into the chamber of the apparatus by urging the predetermined volume of liquid through an outlet of the container and into an inlet of the apparatus from an exterior of the apparatus.

It is understood that the foregoing general description and the following detailed description are exemplary, but are not restrictive, of the invention.

BRIEF DESCRIPTION OF THE DRAWING

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

This invention will now be described with reference to several embodiments selected for illustration in the drawings. It will be appreciated that the scope and spirit of the invention are not limited to the illustrated embodiments. It will further be appreciated that the drawings are not rendered to any particular proportion or scale. Also, any dimensions referred to in the description of the illustrated embodiments are provided merely for the purpose for illustration. The invention is not limited to any particular dimensions, materials, or other details of the illustrated embodiments.

In an exemplary embodiment the present invention provides a kit for draining fluids from the body of a patient. With general reference to the figures, the kit includes an apparatus 10 configured to receive fluids from the body of the patient. The apparatus 10 defines a chamber 13 to contain a predetermined volume of liquid. The apparatus 10 also includes an inlet 16 through which liquid is deliverable to the chamber 13 of the apparatus 10 from an exterior of the apparatus 10. The kit also includes a container 40 packaged with or attached to the apparatus 10. The container 40 is prefilled and sealed, and contains at least the predetermined volume of liquid. The container 40 includes an outlet 47 configured to deliver at least the predetermined volume of liquid to the chamber 13 of the apparatus 10 through the inlet 16 of the apparatus 10.

In another embodiment of the present invention, a method of providing a kit for draining fluids from the body of a patient is provided. The method includes a step of providing an apparatus 10 configured to receive fluids from the body of the patient. The apparatus 10 provided defines a chamber 13 to contain a predetermined volume of liquid. The apparatus provided also includes an inlet 16 through which liquid is deliverable to the chamber 13 of the apparatus 10 from an exterior of the apparatus 10. The method also includes the step of packaging a container 40 with the apparatus 10. The container 40 packaged with the apparatus 10 is prefilled and sealed to contain at least the predetermined volume of liquid. The container 40 packaged with the apparatus also includes an outlet 47 configured to deliver at least the predetermined volume of liquid to the chamber 13 of the apparatus 10 through the inlet 16 of the apparatus 10.

For example, the method of providing recited above may be carried out by a manufacturer, distributor, or other provider of the apparatus and/or container. Alternatively, the method of providing recited above may be carried out by a marketing or sales entity engaged in marketing or selling the apparatus and/or container. Further still, the method of providing recited above may be carried out by a medical professional (for example, in a hospital, clinic, doctor's office, or other facility for medical services). For example, in the case of a medical professional employed at a hospital, a distinct apparatus and container is optionally obtained by the medical professional and subsequently packaged together prior to use. For example, this packaging step may include assembling the apparatus and container into a kit, collecting the apparatus and container on a cart or other location, or simply introducing the apparatus and container into a sterile environment at the same time. As such, any of a number of individuals or entities may engage in the method of providing recited above.

In another exemplary embodiment of the present invention, a method of preparing a system for draining fluids from the body of a patient is provided. The method includes a step of obtaining a kit including an apparatus 10 configured to receive fluids from the body of the patient. The apparatus 10 included in the obtained kit defines a chamber 13 to contain a predetermined volume of liquid. The kit obtained also includes a container 40 packaged with or attached to the apparatus 10. The container 40 is prefilled and sealed to contain at least the predetermined volume of liquid. The method also includes a step of delivering the predetermined volume of liquid from the container 40 into the chamber 13 of the apparatus 10 by urging the predetermined volume of liquid through an outlet 47 of the container 40 and into an inlet 16 of the apparatus from an exterior of the apparatus 10.

According to another exemplary embodiment, the present invention provides a chest drainage system or kit that includes a chest drainage apparatus 10 and a pre-packaged, pre-measured container (e.g., an ampoule) 40 of sterile water or sterile saline or other liquid that can be used by a medical professional to fill a seal chamber 13 of the chest drainage apparatus 10. According to an exemplary embodiment of this invention, the chest drainage system includes an apparatus 10 configured to receive fluids from the body of a patient. The apparatus 10 defines a liquid seal chamber 13 that is sized to contain a predetermined volume of liquid in order to prevent the flow of fluids or gases back toward the patient through the apparatus 10. Liquid is optionally provided in the seal chamber 13 of the apparatus 10 for creating a seal and optionally for detecting air leaks. The apparatus 10 also defines an inlet 16 through which liquid is deliverable to the seal chamber 13 of the apparatus 10 from an exterior of the apparatus 10.

The system according to this invention may also include a container or ampoule 40 that is packaged with the apparatus 10 and that is pre-filled and sealed to contain the predetermined volume of liquid required for the liquid seal chamber 13. The container 40 defines an outlet 47 that is configured to deliver the predetermined volume of liquid to the liquid seal chamber 13 of the apparatus 10 through the inlet 16 of the apparatus 10. The outlet 47 of the container 40 is configured to couple with the inlet 16 of the apparatus 10. In this way, a fluid passageway is formed through which liquid can flow from the container 40 to the liquid chamber 13 of the apparatus 10.

In another exemplary embodiment, the container 40 includes a frangible closure portion 48. When so provided, the removal of the frangible closure portion 48 from the container 40 defines the outlet opening of the container 40.

By providing a pre-packaged, pre-measured container or ampoule 40 of liquid for filling the liquid seal, the present invention provides for quick, dependable and repeatable set-up of the chest drainage apparatus 10. Further, the invention eliminates the problem of finding water or another suitable liquid for the liquid seal outside the operating room (OR) environment. Further still, according to an exemplary embodiment, the invention helps to prevent overfilling of the liquid seal chamber 13 and helps to eliminate any need for readjustment of the liquid level in the liquid seal chamber 13. An additional benefit of the invention is that it helps to eliminate the use of syringes or needles that may otherwise be needed for filling the liquid seal chamber 13 or adjusting the level of the liquid in the liquid seal chamber 13.

In yet another exemplary embodiment of the present invention, the chest drainage apparatus 10 of the chest drainage system is provided with an inlet 16 in the form of a needleless access port.

Figure 5:
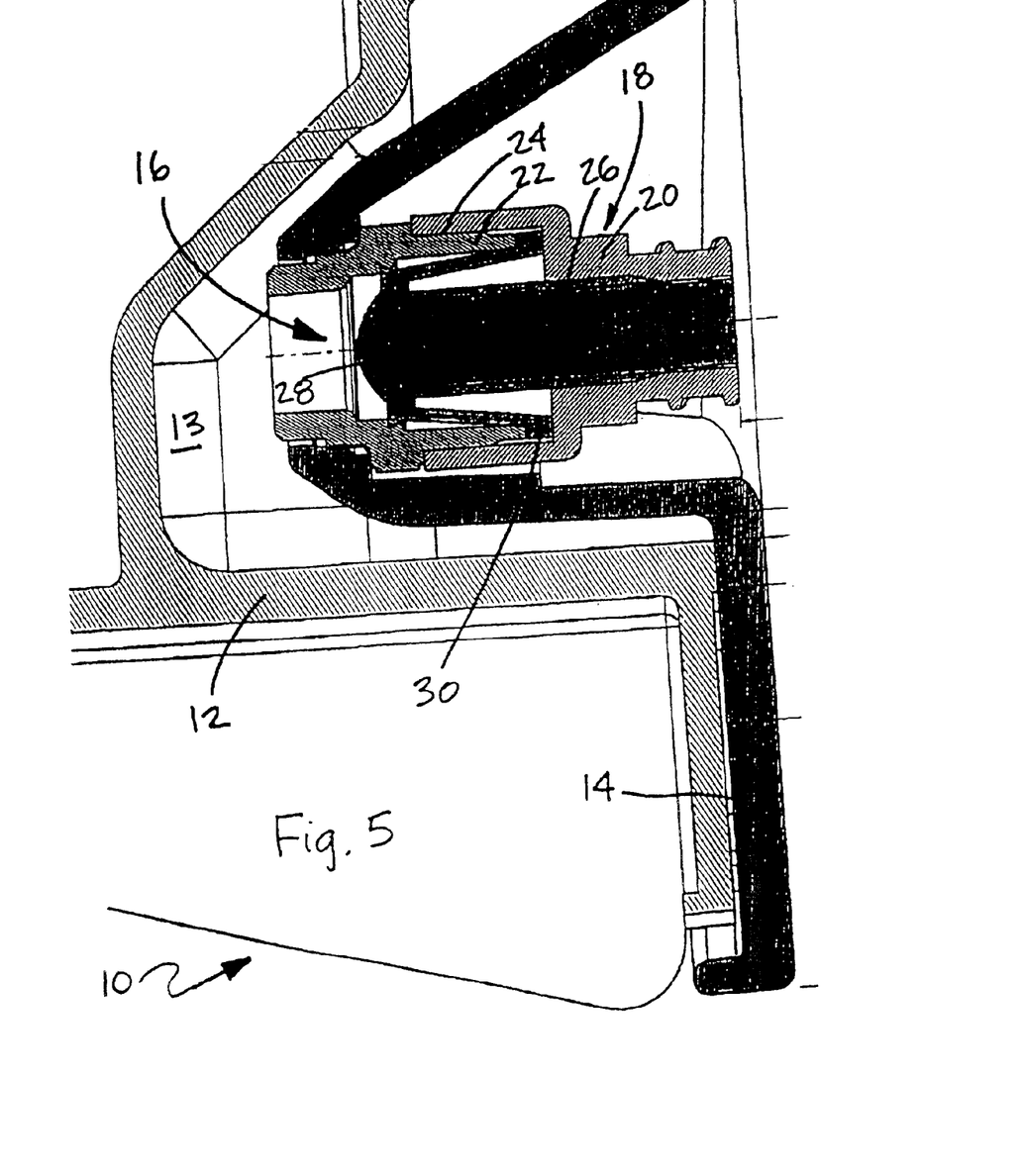
FIG. 5 is a partial cross-sectional view of a chest drain in accordance with an exemplary embodiment of the present invention.

Referring to the exemplary embodiment illustrated in FIG. 5, for example, a chest drainage apparatus 10 includes a body 12 and a cover 14 mounted to the body 12. A water seal chamber 13 is defined in the space between the body 12 and the cover 14. A needleless access port 16 is mounted to the cover 14 or body 12 to provide access to the water seal chamber 13.

The needleless access port 16 includes a luer connector 18 that is attached to the cover 14. The luer connector 18 in turn includes a front portion 20 and a rear portion 22 that is connected to the front portion 20 by means of a weldment or adhesive bond 24, for example. A plastic support 26 is mounted within the luer connector 18. An elastomeric seal valve 28 is mounted within the luer connector 18 and the support 26, and a flange portion 30 of the seal valve 28 is captured between the front portion 20 and back portion 22 of the luer connector 18.

Figure 6:
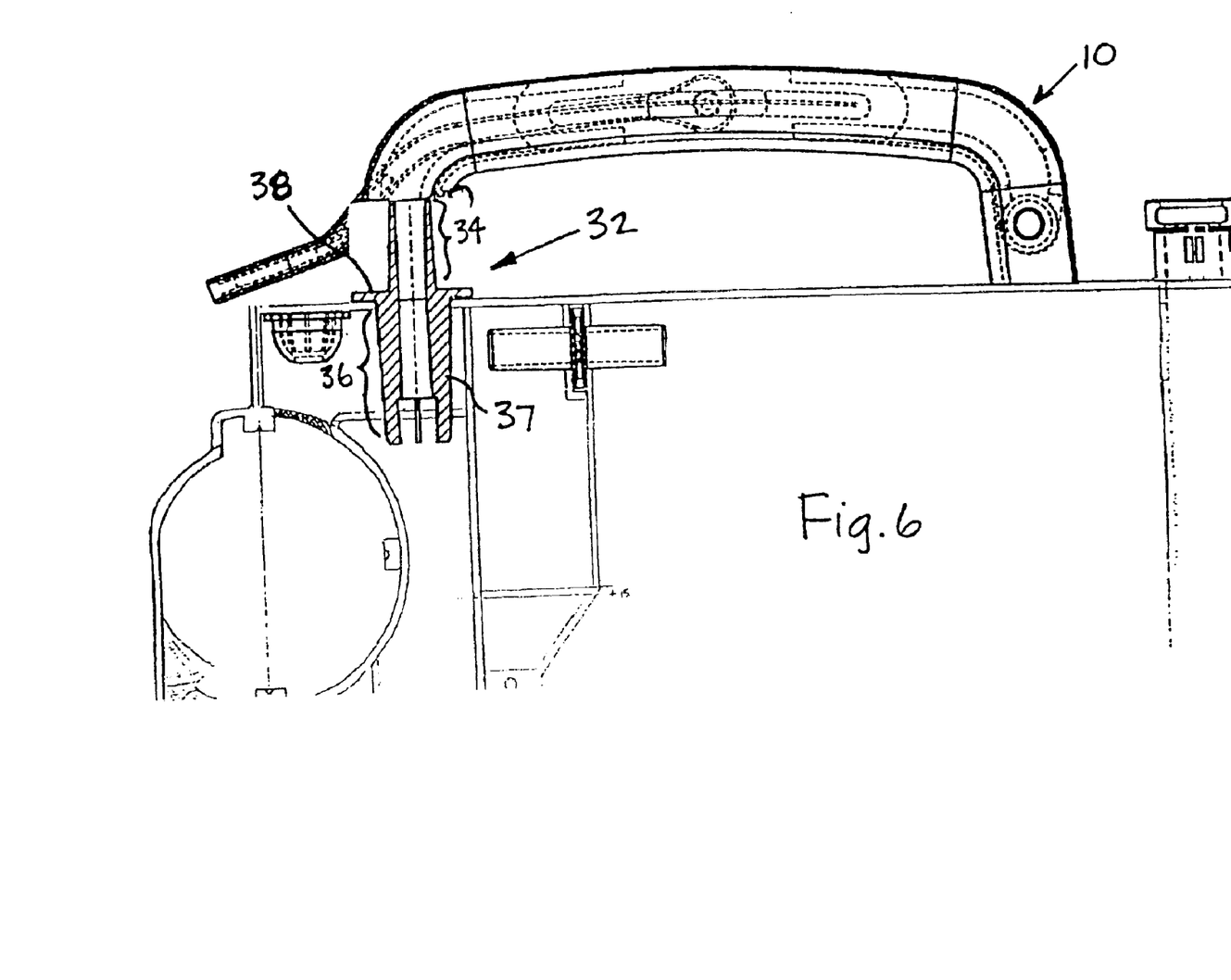
FIG. 6 is a partial front view of a chest drain in accordance with an exemplary embodiment of the present invention.

Alternatively, access for the introduction of water or other liquid into a water seal chamber 13 can be provided through the top of a chest drainage apparatus 10 by means of an alternative inlet port. Referring to FIG. 6, for example, a suction connection nozzle 32 is mounted in an opening in the top of the chest drainage apparatus 10 for the connection of the chest drainage apparatus 10 to a source of suction (not shown). The nozzle 32 can also be used for the introduction of water into the water seal chamber 13. Although shown as a separate component in FIG. 6, the nozzle 32 can also be integrally molded into the body 12 of the apparatus 10.

An exemplary nozzle 32 includes a port portion 34 into which water or another liquid can be introduced into the apparatus 10. The nozzle 32 also includes a mounting portion 36, which extends through an opening in the apparatus 10. A flange portion 38 separates the mounting portion 36 and the port portion 34 of the nozzle 32. A series of ribs 37 may extend along the mounting portion 36 of the nozzle 32.

Figure 7:
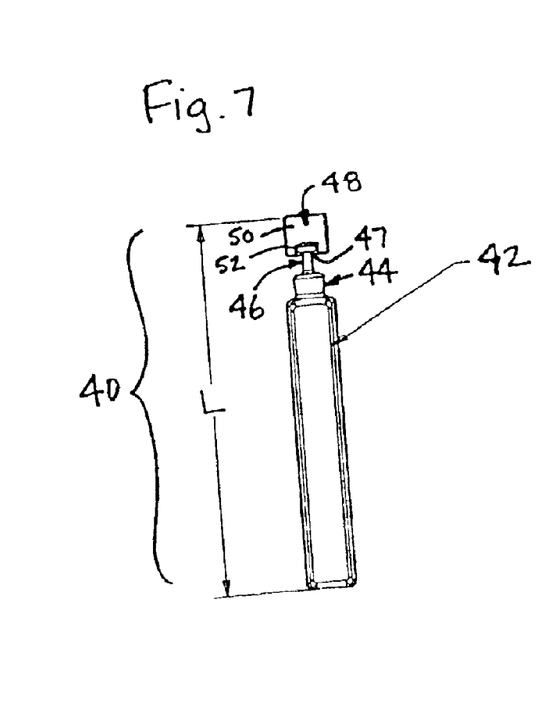
FIG. 7 is a front view of a container in accordance with an exemplary embodiment of the present invention.
Figure 8:
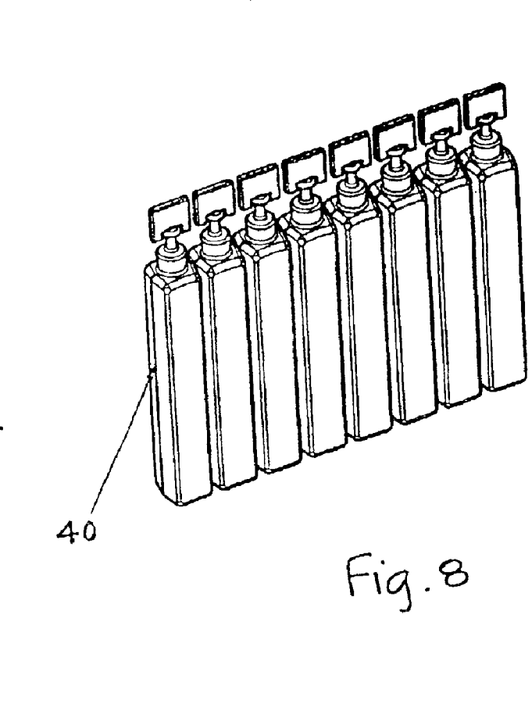
FIG. 8 is a perspective view of multiple containers in accordance with an exemplary embodiment of the present invention.
Figures 9A, 9B:
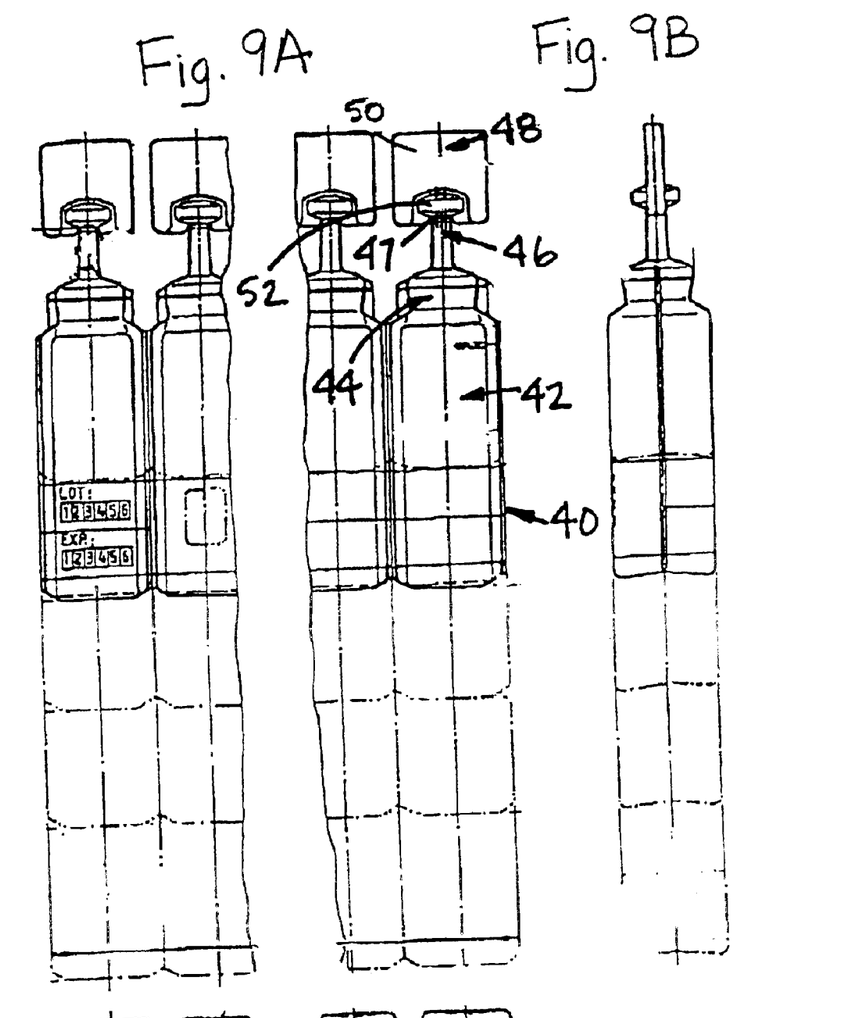
FIG. 9A is a partial front view of the containers shown in FIG. 8.
FIG. 9B is a side view of the containers shown in FIG. 8.
Figure 9C:
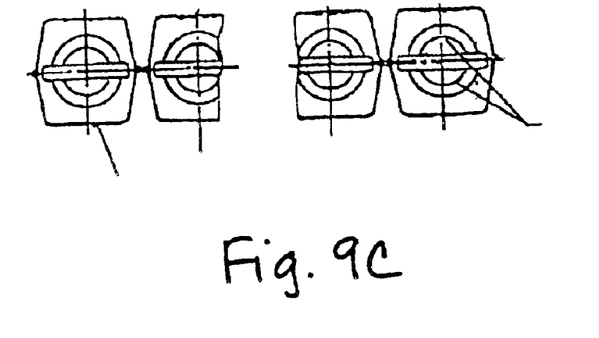
FIG. 9C is a partial top view of the containers shown in FIG. 8.

Exemplary embodiments of pre-packaged, pre-measured containers or ampoules 40 of sterile water or sterile saline or other liquid, suitable for use as a component of the chest drainage system or kit according to this invention, are illustrated in FIGS. 7–9. As will be described later, the containers or ampoules 40 are adapted for introducing liquid into the liquid seal chamber 13 of the apparatus 10 of the system or kit through an inlet formed in the apparatus 10.

Referring to FIG. 7, one exemplary embodiment of a container 40 is illustrated. Container 40 includes an elongated body portion 42, a neck portion 44 at the top of the body portion 42, a nozzle portion 46 extending from the neck portion 44, and a closure portion 48 above the nozzle portion 46. The body portion 42 of the container 40 is configured to contain a pre-determined volume of liquid. For example, the body portion 42 can be sized to contain 35 ml of liquid, 45 ml of liquid, or any volume of liquid corresponding to the desired fill volume for the liquid seal chamber 13 of the apparatus 10 with which the container 40 is intended to be used.

As will be described in further detail later, the liquid may be completely or partially emptied from the container 40 into the seal chamber 13 of the apparatus 10. The provision of a pre-determined volume of liquid in the container 40 helps to ensure that the liquid seal chamber 13 is not overfilled or underfilled. The provision of a predetermined volume of liquid also eliminates the need on behalf of medical professionals to procure a source of liquid and to introduce a measured quantity of liquid into the apparatus 10. Additionally, the provision of a pre-determined volume of liquid helps to eliminate the need on behalf of medical professionals to use a syringe or needle to withdraw any excess liquid from an overfilled seal chamber 13. Alternatively, the container may be filled with an amount of liquid that exceeds the pre-determined volume.

In an exemplary embodiment of the present invention, the container 40 may be formed of a non-rigid or collapsible material. Alternatively, the container 40 may be formed from a rigid material. For example, the container 40 may be formed from polyethylene, polypropylene, or from any commonly formed materials. For example, the container 40 may be molded or pre-formed. Other plastics and non-plastic materials and forming methods are contemplated as well.

In an exemplary embodiment of the present invention, the container 40 is filled with sterile/non-pyrogenic water; however, any liquid or material that adequately seals the seal chamber 13 may be used.

The container 40 may be blow-molded with a wall thickness selected to provide the container 40 with sufficient strength such that it is self-supporting. In other words, the container 40 may have a wall that is thick enough so that the container 40 will hold its shape. On the other hand, the container 40 may have a wall thickness selected to allow a medical professional to squeeze the contents of the container 40 from its body portion 42 and through its nozzle portion 46 by collapsing the wall of the body portion 42. When the container 40 is formed from a plastic material such as polyethylene, the container's body portion 42 may have a wall thickness less than about 0.1 inch, and in an exemplary embodiment between about 0.015 inch and about 0.030 inch, and in another exemplary embodiment about 0.020 inch; however, any wall thickness can be selected based on design parameters and preferences. The container 40 may optionally be provided with a luer nozzle neck at nozzle portion 46.

The container 40 can alternatively be formed from a flexible thickness of material to form a bag-like ampoule. A portion of such a bag-like ampoule can be torn away or otherwise manipulated to open an outlet port through which water or another liquid can be discharged.

For example, the closure portion 48 of the container 40 may have a separable, frangible cap that can be twisted to break the closure portion 48 away from the nozzle portion 46, thereby forming an outlet 47 at the juncture between the nozzle portion 46 and the closure portion 48. Upon removal of the closure portion 48 from the nozzle portion 46, the so-formed outlet 47 permits a medical professional to discharge the contents of the body portion 42 from the container 40 by squeezing, deforming, or reorienting the wall of the container's body portion 42. The closure portion 48 includes a flange-shaped portion 50 that can be gripped by a medical professional so that the closure portion 48 can be rotated with respect to the body portion 42 of the container 40. The closure portion 48 is rotated or otherwise deformed in order to break the connection between the closure portion 48 and the nozzle portion 46. The closure portion 48 also includes a receptacle portion 52, the bottom of which is integrally and removably connected to the top of the nozzle portion 46.

Although the closure portion 48 may be provided in any of a number of forms such as a threaded cap, a snap fit, a hinged lid, or other closure configurations, the closure portion 48 may alternatively be integrally formed with the remainder of the container 40 by a blow-molding process, and the removal of the closure portion 48 would occur when the wall material of the container 40 is broken or torn. The closure portion 48 produces an opening in the form of the outlet 47 when it is removed.

As shown in FIG. 8, multiple containers or bottles 40 may be formed in a molded group such as the group of eight (8) containers 40 illustrated.

Additional views of a group of containers or bottles 40 are shown in FIGS. 9A, 9B, and 9C. As shown in FIGS. 7 and 9A, the containers 40 can be provided with a length "L" selected to provide a desired, pre-determined volume. The dotted lines in FIG. 9A illustrate that the containers 40 can be provided in five (5) different lengths "L", although it should be understood that the container 40 can be provided in any desired length, shape, and size.

One example of a container 40 suitable for use as a component of the chest drainage system or kit of this invention is available under the trademark BOTTELPACK from Rommelag USA Inc., of Edison, N.J. Such containers 40 may be formed from polyethylene or polypropylene although other plastics and non-plastics can be used. Such containers 40 can be blow molded, filled, and sealed in one automated machine, and such machines are also available from Rommelag USA Inc.

Although an exemplary closure embodiment is illustrated in the figures, the container can be provided with any of a wide variety of closures, as discussed above. In other words, the twist-off frangible closure 48 described above is only one example of a suitable closure. A cutting ring closure, wherein a ring inside the cap cuts a large opening into the top of the container, may also be used. A screw cap/pin arrangement may also be utilized wherein turning down the cap with the pin results in an opening. A Euro-closure can also be used to combine hermetically sealed containers with a Euro-cap. Other closure configurations are contemplated as well.

The container 40 can be provided with a wide variety of other outlet openings as well. For example, fluid dispensing closures suitable for use with a chest drainage system according to this invention include those disclosed by Dark in U.S. Pat. Nos. 4,440,327 and 5,392,968, which are incorporated herein by reference.

The body portion 42 of the container 40 can have a substantially rectangular or polygonal cross-sectional shape (as shown in FIG. 9c), or a cylindrical or another shape can be provided as well. Also, a bellows or accordion design can be used for the body portion 42 to assist in its collapse as its contents are emptied by a medical professional.

According to another exemplary aspect of the invention, the container or ampoule 40 is attached or otherwise fixed to the apparatus 10 so that the container 40 is always conveniently accessible to medical professionals that use the system or kit. The container 40 can be attached to the apparatus 10 by a wide variety of attachment means including, but not limited to, tape that is used to hold the container 10 against a surface of the apparatus 10, a receptacle or other engagement structure provided on or with the apparatus 10 to receive or otherwise engage the container 40 or a portion thereof, VELCRO or other hook and loop fasteners, clips, pouches, and/or an adhesive that is used to temporarily bond the container 40 to the apparatus 10. If a receptacle or other engagement structure is used, the structure can be a holder formed as part of the apparatus 10, a bag attached to the apparatus 10 for receiving the container 40, or a pocket or insert provided on the apparatus 10, or a flange system positioned to receive the container 40, for example.

Figure 10:
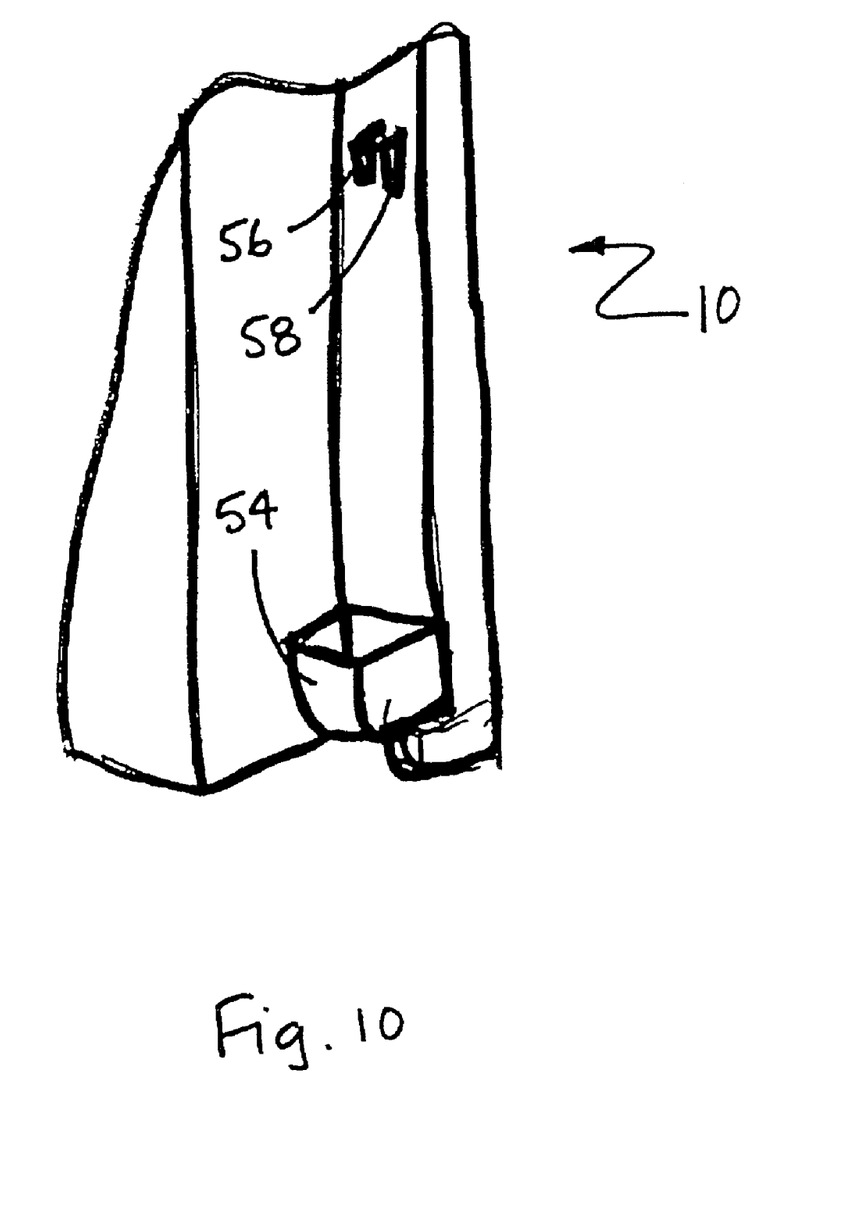
FIG. 10 is a partial perspective view of an apparatus including a receptacle for receiving a container in accordance with an exemplary embodiment of the present invention.

An example of a receptacle that can be provided on the apparatus 10 for receiving the container 40 is shown in FIG. 10. In the receptacle embodiment illustrated in FIG. 10, a portion of a surface of the apparatus 10 is provided with a molded or otherwise-formed or attached holder 54, which acts as a receptacle or cradle to receive a bottom portion of the body portion 42 of the container 40. A pair of detents 56, 58 are optionally provided along the surface of the apparatus 10 above the holder 54. The detents 56, 58 are spaced and configured to releasably engage an upper portion of the container 40. For example, the detents 56, 58 can be configured to provide an interference or snap-fit engagement for the nozzle portion 46 of the container 40. The detents 56, 58 can be employed to the exclusion of the holder 54 and vice versa. Also, either the detents 56, 58 or the holder 54 can be used alone or in combination with other attachment means.

Figure 11A:
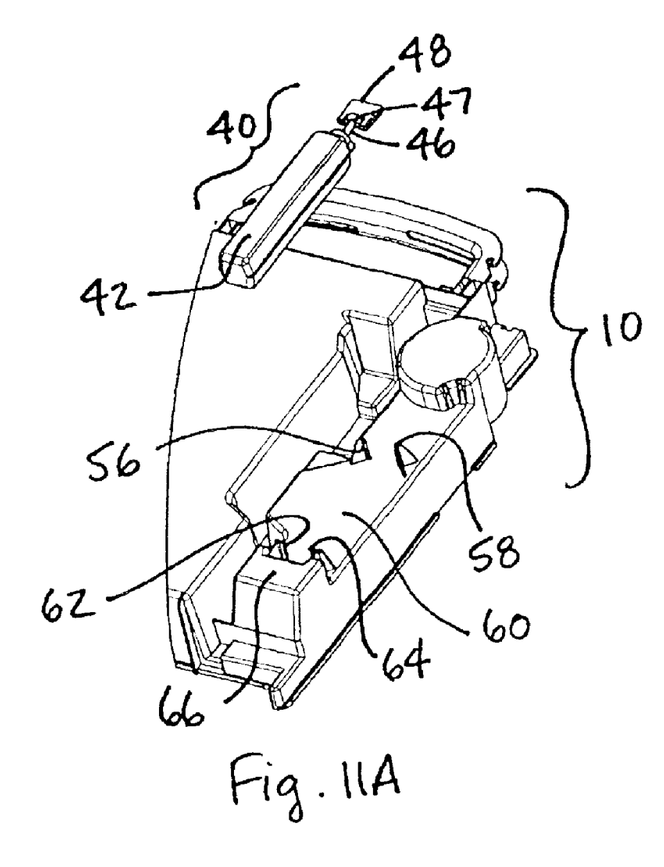
FIG. 11A is a partial, exploded perspective view of an embodiment of an apparatus assembly including a container and another exemplary embodiment of a receptacle for receiving a container.
Figure 11B:
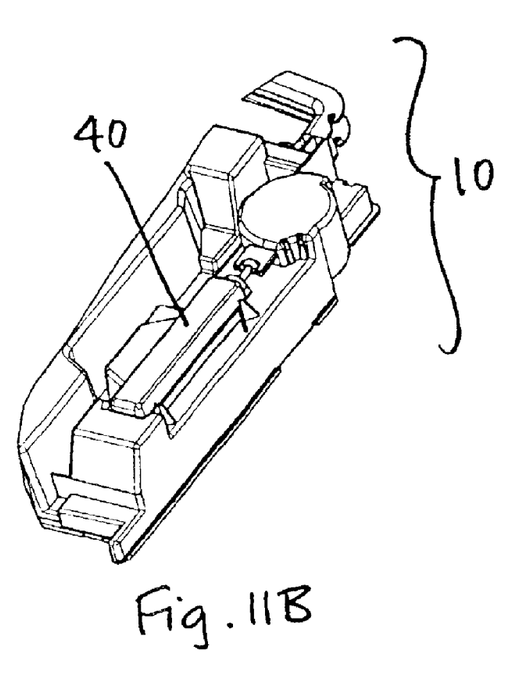
FIG. 11B is a partial perspective view of the apparatus assembly illustrated in FIG. 11A.

FIGS. 11A and 11B provide illustration of another holder for a container 40 that is formed into or attached to the apparatus 10. For example, referring to FIG. 11A, a portion of the back of an apparatus 10 is shown. Apparatus 10 includes a receptacle 60 formed as a part of the back of apparatus 10. Receptacle 60 is defined by wall section 66, and detent surfaces 56, 58, 62 and 64. Container 40 is also illustrated in FIG. 11A, including body portion 42, closure portion 48, nozzle portion 46, and outlet 47.

FIG. 11B illustrates container 40 received by receptacle 60. As such, a bottom area of container 40 rests against or adjacent an optional wall section 66, while the sides of body portion 42 are held substantially in place by detents 56, 58, 62 and 64. The detents illustrated in FIGS. 11A and 11B extend outwardly from the rear surface of the apparatus. Alternative, one or more of the engagement surfaces may be provided in a recess formed in the apparatus.

Alternatively, the container 40 can be provided or packaged together with the apparatus 10 as a component of the system or kit without being attached to the apparatus 10. For example, the system or kit illustrated in the figures provides a substantially self-sufficient kit that is packaged in such a way that it includes a chest drainage apparatus 10 and a source of liquid in the form of the container 40 for filling the water seal chamber 13 of the apparatus 10. The container 40 is therefore conveniently provided for use by a medical professional whether or not it is physically attached to the apparatus 10 or merely packaged together or otherwise provided with the apparatus 10.

In use and during set-up, the water seal chamber 13 of the apparatus 10 is filled using the water or other liquid provided in the container 40. More specifically, after the container 40 is opened, the outlet of the container 40 (e.g., the outlet 47) is mated or coupled with the inlet of the apparatus (e.g., the needleless valve port 16 or the suction nozzle 32).

If a fluid is to be introduced into the water seal chamber 13 via the suction nozzle 32, the nozzle portion 46 of the container 40 may be inserted into the port portion 34 of the nozzle 32 such that the outlet 47 of the container 40 directs water flow into the interior of the nozzle 32. The water will then flow into the water seal chamber 13. There need be no seal or close fit between the port portion 34 of the nozzle 32 and the nozzle portion 46 of the container because the water will tend to flow downwardly into the nozzle 32 even if there are significant gaps between the outer surface of the nozzle portion 46 and the inner surface of the port portion 34.

If water is to be introduced into the water seal chamber 13 via the needleless valve port 16, the nozzle portion 46 of the container 40 may be inserted into the front portion 20 of the luer connector 18 such that the outlet 47 of the container 40 directs water flow into the interior of the luer connector 18. The water will then flow into the water seal chamber 13. More specifically, the tip of the nozzle portion 46 of the container 40 at least partially deforms the seal valve 28 as the nozzle portion 46 is inserted into the luer connector 18. By doing so, the slit in the seal valve 28 is opened to define a flow path extending from the outlet 47 of the container 40 to the water seal chamber 13. Although there need be no seal between the front portion of the luer connector 18 and the nozzle portion 46 of the container 40, a close fit between the outer surface of the nozzle portion 46 and the inner surface of the luer connector 18 may be provided. The outlet of the container 40 and the inlet of the apparatus 10 are optionally configured to form such a close fit to discourage leakage of water through the space between adjacent surfaces of the container 40 and the apparatus 10.

Although the exemplary embodiments of the container's nozzle portion 46, the suction nozzle port 32, and the needleless port 16 illustrated in the figures include a male-female mating configuration between the nozzle portion 46 and the ports in that the nozzle extends into the ports, other configurations are contemplated as well. For example, face-to-face mating, female-male, threaded engagement, and other couplings can also be selected.

Although the container 40 has been described as a supply of liquid for the water seal chamber 13 of the chest drainage apparatus 10 of the system disclosed herein, it is also contemplated that the container 40, or an additional container provided therewith, can be used as a supply of liquid for one or more other portions of the apparatus 10. For example, if water or another liquid is utilized for suction control or regulation within a chamber of the apparatus 10 (as opposed to dry suction control), then another container such as container 40 can be provided with the apparatus 10 for supplying liquid to the suction control chamber of the apparatus 10.

Although illustrated and described herein with reference to certain specific embodiments, the present invention is nevertheless not intended to be limited to the details shown. Rather, the modifications set forth herein and various additional modifications may be made within the scope and range of equivalence of the claims and without departing from the spirit of the invention.

What is claimed:

1. A kit for draining fluids from the body of a patient, said kit comprising:
    an apparatus configured to receive fluids from the body of the patient and defining a chamber to contain a predetermined volume of liquid, said apparatus having an inlet through which liquid is deliverable to said chamber of said apparatus from an exterior of said apparatus; and
    a container packaged with or attached to said apparatus, said container being prefilled and sealed to contain at least said predetermined volume of liquid, said container having an outlet configured to deliver at least said predetermined volume of liquid to said chamber of said apparatus through said inlet of said apparatus.

2. The kit of claim 1, wherein said container comprises a frangible closure portion, wherein removal of said frangible closure portion from said container facilitates flow of liquid through said outlet.

3. The kit of claim 1, wherein said predetermined volume of liquid in said chamber substantially prevents air from flowing back to the patient.

4. The kit of claim 1, wherein said predetermined volume of liquid, when delivered to said chamber, facilitates detection of air leaks.

5. The kit of claim 1, wherein said predetermined volume of liquid, when delivered to said chamber, facilitates suction control.

6. The kit of claim 1, wherein said container is a preformed container.

7. The kit of claim 1, wherein said container is attached to said apparatus using any of a receptacle formed on the apparatus, tape, adhesive, a hook and loop fastener, and a clip.

8. The kit of claim 1, wherein said container contains sterile water or sterile saline.

9. The kit of claim 1, wherein an outlet portion defining said outlet of said container is configured to couple with the inlet of said apparatus.

10. The kit of claim 1, wherein said container is formed from a plastic material.

11. The kit of claim 10, wherein said container is formed from from polyethylene.

12. The kit of claim 1, further comprising means for attaching said container to said apparatus.

13. The kit of claim 12, wherein said attaching means is provided as a component of said apparatus.

14. A method of providing a kit for draining fluids from the body of a patient comprising the steps of:

provic ing or obtaining an apparatus configured to receive fluids from the body of the patient and defining a chamber to contain a predetermined volume of liquid, the apparatus having an inlet through which liquid is deliverable to the chamber of the apparatus from an exterior of the apparatus; and packaging a container with the apparatus, the container being prefilled and sealed to contain at least the predetermined volume of liquid, the container having an outlet configured to deliver at least the predetermined volume of liquid to the chamber of the apparatus through the inlet of the apparatus.

15. The method of claim 14 wherein said packaging step comprises attaching the container to the apparatus.

16. The method of claim 15 wherein, in the packaging step, the container is attached to the apparatus using any of a receptacle formed on the apparatus, tape, adhesive, a hook and loop fastener, and a clip.

17. A method of preparing a system for draining fluids from the body of a patient comprising the steps of:

obtaining a kit including an apparatus configured to receive fluids from the body of the patient and defining a chamber to contain a predetermined volume of liquid, the kit also including a container packaged with or attached to the apparatus, the container being prefilled and sealed to contain at least the predetermined volume of liquid; and delivering the predetermined volume of liquid from the container into the chamber of the apparatus by urging the predetermined volume of liquid through an outlet of the container and into an inlet of the apparatus from an exterior of the apparatus.

18. The method of claim 17 further comprising the step of: detaching the container from the apparatus.

19. The method of claim 17 further comprising the step of: removing a frangible closure portion from the container, thereby opening the outlet of the container.

20. The method of claim 17 further comprising the step of: coupling the outlet of the container to the inlet of the apparatus.

21. The method of claim 17 further comprising the step of: collapsing at least a portion of the container to urge the predetermined volume of liquid into the chamber of the apparatus through an outlet of the container and into an inlet of the apparatus from an exterior of the apparatus.

* * * * *